US007008390B2

(12) United States Patent
Miotto et al.

(10) Patent No.: US 7,008,390 B2
(45) Date of Patent: Mar. 7, 2006

(54) PERFORATING VEIN MASSAGE DEVICE

(75) Inventors: Onorio Miotto, Trev (IT); Axel Kubelka, Vienna (AT)

(73) Assignee: Evoluzione S.R.L., Trev (IT)

( * ) Notice: Subject to any disclaimer, the term of this patent is extended or adjusted under 35 U.S.C. 154(b) by 0 days.

(21) Appl. No.: 10/935,487

(22) Filed: Sep. 7, 2004

(65) Prior Publication Data

US 2005/0054961 A1 Mar. 10, 2005

Related U.S. Application Data

(63) Continuation-in-part of application No. 10/262,535, filed on Oct. 1, 2002, now abandoned, which is a continuation of application No. PCT/AT01/00094, filed on Apr. 2, 2001.

(30) Foreign Application Priority Data

Apr. 3, 2000 (AT) .................................. 559/2000

(51) Int. Cl.
*A61F 5/00* (2006.01)

(52) U.S. Cl. ............................ 602/23; 602/27; 602/65; 602/13; 128/882

(58) Field of Classification Search ................ 128/869, 128/882, DIG. 20; 2/22; 623/27, 28, 29, 623/47; 602/23, 27, 28, 29, 30, 60, 61, 62, 602/65, 66, 13, 16

See application file for complete search history.

(56) References Cited

U.S. PATENT DOCUMENTS

| | | | | |
|---|---|---|---|---|
| 4,628,945 | A * | 12/1986 | Johnson, Jr. | 128/DIG. 20 |
| 4,844,094 | A * | 7/1989 | Grim | 602/27 |
| 4,977,891 | A | 12/1990 | Grim | 128/80 |
| 5,099,860 | A | 3/1992 | Amrein | 128/882 |
| 5,348,530 | A | 9/1994 | Grim et al. | 602/13 |
| 5,366,439 | A * | 11/1994 | Peters | 602/13 |
| 5,527,269 | A * | 6/1996 | Reithofer | 602/27 |
| 5,711,760 | A | 1/1998 | Ibrahim et al. | 601/149 |
| 5,893,219 | A | 4/1999 | Smith et al. | 36/3 |
| 6,022,331 | A * | 2/2000 | Darcey | 602/12 |
| 6,056,712 | A * | 5/2000 | Grim | 602/27 |
| 6,129,688 | A | 10/2000 | Arkans | 601/152 |
| 6,689,081 | B1 * | 2/2004 | Bowman | 602/27 |
| 6,767,332 | B1 * | 7/2004 | Pardue et al. | 128/882 |

* cited by examiner

*Primary Examiner*—Fadi H. Dahbour
(74) *Attorney, Agent, or Firm*—Thomas R. Vigil; Welsh & Katz, Ltd.

(57) ABSTRACT

The device for massaging a lower leg comprises a base pad (2) arranged in an area of the sole and a bladder (1) arranged in the region of the lower leg. A tubular connection is provided between the inner spaces of the base pad (2) and of the bladder (1). A frame (8) comprising a base part (12) and at least one side part (13, 7) projects upward from the tubular connection. The frame is mountable inside a shoe with the bladder (1) being fastened to the side part and the bladder (1) being positioned on the frame (8) in such a manner that it comes to lie above the perforating vein in the ankle area. A pressure is exerted by the bladder (1) onto the leg through the body weight applied to the base pad (2) when the foot is loaded.

12 Claims, 2 Drawing Sheets

PERFORATING VEIN MASSAGE DEVICE

CROSS REFERENCE TO RELATED APPLICATIONS

This application is a continuation-in-part application of U.S. patent application Ser. No. 10/262,535 filed Oct. 1, 2002 now abandoned, which is a continuation of PCT/AT01/00094 filed Apr. 2, 2001, which claims the benefit of priority from Austrian Patent Application No. 559/2000, filed Apr. 3, 2000.

BACKGROUND OF THE INVENTION

1. Field of the Invention

The present invention relates to a device for massaging a lower leg comprising a base pad arranged in an area of the sole and a bladder arranged in the region of the lower leg, a tubular connection being provided between the inner spaces of the base pad and of the bladder.

2. Description of the Prior Art

Devices for the treatment of hypostatic leg conditions such as varicose veins, chronic phlebitis, chronic venous insufficiencies as well as for the aftertreatment and prevention of thrombosis are becoming increasingly important as a result of the wide occurrence of such diseases. In these diseases, the blood pumped toward the heart rushes back as a result of the change occurred in the veins. As these anatomic changes are irreversible, the permanent reflux increasingly causes the blood to stagnate in the damaged veins of the lower leg. This stagnation causes the blood to pass through the veins into the surrounding muscles, which harden as a result thereof. The increasingly hardened muscles are not capable of exerting an elastic pressure onto the congested veins and cannot force the blood upwards toward the heart.

These anatomic changes result in permanent functional disorders in the form of an increasing fluid stagnation and of an external swelling of the lower legs. In order to prevent or cure these functional disorders by means of internal or external treatment, other methods have been tried such as the wearing of compression stockings; bandages and insole supports; scierotherapy and surgery, as well as infusions.

The documents DE-OS 195539, FR-OS 2108764, DE 3440638 A1, DE 2122907 B2 and CH 618 879 A5 describe devices that enclose the entire lower leg and massage this area by exerting a pressure, thus assisting the venous return of the blood. The disadvantage of the devices mentioned is not only the irksome procedure for a patient of putting it on to the leg but also the fact that the entire lower leg is being massaged, which requires a very efficient pressure source with a high energy need. An appropriate, efficient pressure source, a pressure pump for example, may strongly limit the freedom of movement of a patient because of its size or the size of its energy source, an accumulator for example. Also, with such devices, the duration of the therapeutic effect is limited by the life of the energy source.

WO 90/09115 describes footwear provided with an upper in which a bladder filled with a fluid is arranged, the bladder communicating with a pump by way of a regulator, the regulator being configured to maintain the pressure generated by the pump constant within the bladder. The footwear is said to provide optimal hold and optimal support for a foot. For this reason, the bladder substantially completely encompasses the instep and the ankle area of the foot. With this footwear, which provides a constant pressure exerted over a large area of the foot, it is not possible to exert a pulsating pressure that assists on purpose the blood return to the heart.

U.S. Pat. No. 5,366,439 A discloses an ankle brace intended to prevent ankle injury. This ankle brace is provided with a frame with a heel stirrup provided with a lower portion and with inner and outer upright portions that are oriented substantially parallel to the lower leg. The inner lateral portions are provided with a vinyl bubble film as it is known for example in the packaging sector, the inner portions being pressed by the outer portion against areas of the lower leg and of the ankle.

This ankle brace is not suited for the treatment of hypostatic leg conditions as its design does not permit to enhance the flow of blood toward the heart. In putting on the ankle brace very tightly, the blood may be prevented from flowing into the foot but this has the disadvantage that the blood may stagnate above the ankle. From a therapeutic point of view, it is not indicated to cause blood to stagnate above the ankle area with hypostatic leg conditions, as this generally increases the stagnation pressure in the veins, which may increasingly cause blood to pass from the veins into the surrounding muscle tissue.

U.S. Pat. No. 5,353,525 A discloses an athletic shoe which is provided, in the heel area of its sole, with a flat pump chamber communicating with inflatable bladders which are arranged in the upper portion of the shoe in such a manner that they support the instep and the ankle. In order not to generate too high a pressure in the bladders, valves are provided which open when the pressure exceeds a predetermined threshold pressure and permit air to exit the bladders. The shoe described serves to protect the foot and ankle area when the user is active. It is particularly intended to prevent ankle strain. Like in the above mentioned WO 90/09115, this shoe is not suited to enhance the venous blood circulation as with this design it is not possible to exert on purpose a pressure onto the veins or onto such locations in the foot or the ankle area that make sense from a therapeutical point of view.

Not the least reason why the devices disclosed in the three last mentioned documents are not suited for the treatment of hypostatic leg conditions is that the object of these inventions is to protect the foot and ankle area, more specifically during sport activities.

BRIEF SUMMARY OF THE INVENTION

It is an object of the present invention to assist the physiological and functional functions of the lower leg contributing to the circulation of venous blood by forcing it upward and to avoid the disadvantages of the devices mentioned herein above.

In accordance with the invention, the solution to this object is achieved with a device of the type mentioned herein above in providing a frame composed of a base part and of at least one side part projecting upward therefrom, the frame being mountable inside a shoe, the bladder being fastened to the side part and being positioned on the frame in such a manner that it comes to lie above the perforating vein in the ankle area, a pressure being exerted by the bladder onto the leg through the body weight applied to the base pad when the foot is loaded.

Venous blood circulation in the legs may also be encouraged in that a bladder is fastened in the side part of a shoe located on the inner side of the lower leg and in that the bladder is positioned within the shoe in such a manner that it lies above the perforating vein in the ankle area, a pressure being exerted by the bladder onto the leg through the body weight applied to the base pad when the foot is loaded.

Due to its valve function, the perforating vein plays a particular part in the venous blood circulation in the legs. Many vein ailments are caused by a failure of this valve function. Assisting the perforating vein in its venous valve function by exerting a rhythmic pressure in synchronism with the walking movement may result in a decisive alleviation of vein ailments in the legs. In the prevention of vein ailments also, assisting the function of the perforating vein by exerting a rhythmic pressure proved to make sense.

In order to allow the base pad to regenerate as fast and completely as possible, an advantageous embodiment consists in having a resilient space holder enclosed within the base pad, the space holder increasing the working volume within the base pad when the foot is unloaded, causing the bladder to collapse correlative to the displacement of volume.

Good mechanical properties are achieved when the resilient space holder is made of open pore foam.

In an advantageous embodiment, the bladder, the base pad and the tubular connecting piece located therebetween are made in one piece.

In order to facilitate the fastening of the bladder on the frame it proves advantageous to have a pocket arranged on the bladder and/or on the tubular connecting piece on the surfaces thereof that are turned away from the foot, the pocket being capable of receiving the side part.

In an advantageous embodiment the side part is configured to form a U-shaped bar extending upward from the base part.

The device may be stowed in a relatively compact space thanks to its foldable side part.

In order to allow pressure adjustment within the bladder, an advantageous embodiment is realized in such a manner that a fluid may enter and/or exit the bladder, the base pad and the tubular connecting piece through a valve located on the side of the bladder turned away from the foot.

To fixate the bladder it proved advantageous to provide a bore for receiving the valve and, as a result thereof, for fixating the bladder on the frame, in the upper region of the side part.

For great freedom in configuration it proved advantageous to have the bladder, the base pad and the tubular connection therebetween made of a foil bondable plastic material.

The fixation of the frame onto the leg is facilitated in providing the frame with an elastic tape which is arranged in the upper region of the side part and is fastenable to the lower leg by means of a closure.

According to one of the teachings of the present inventions there is provided a device for massaging a lower leg for treating hypostatic leg conditions and for preventing stagnation of blood in the leg, comprising a base pad having inner spaces and being arranged in an area of a sole of a foot and a bladder arranged in the region of the lower leg, a tubular connection being provided between the inner spaces of the base pad and of the bladder, a working fluid in one of the inner spaces of the pad or the bladder, the bladder being fastened in the side part of a shoe located on the inner side of the lower leg and the bladder is positioned within the shoe in such a manner that it covers the lower leg only above a location at which a perforating vein emerges beneath the muscles on the rear inner side of the ankle, so that a person wearing the device and while walking will exert a pressure on the pad which will periodically inflate the bladder with the working fluid and place periodic pressure just on the location of the lower leg.

Further, according to another teaching of the present invention, there is provided a device for massaging a lower leg for treating hypostatic leg conditions and for preventing stagnation of blood in the leg comprising a base pad arranged in an area of a sole of a foot and having inner spaces and a bladder arranged in the region of the lower leg, a tubular connection including at least one side part extending between the inner spaces of the base pad and the bladder, a working fluid in one of the bladder or the inner spaces of the base pad, a frame comprising a base part and the at least one side part projecting upward from the base part, the frame being mountable inside a shoe, the bladder being fastened to the side part and the bladder being positioned on the frame in such a manner that it covers the lower leg only above a location at which a perforating vein emerges beneath the muscles on the rear inner side of the ankle, so that a person walking while wearing the device will periodically exert a pressure on the pad causing working fluid to inflate the bladder and place periodic pressure just on the location of the lower leg.

BRIEF DESCRIPTION OF THE SEVERAL VIEWS OF THE DRAWINGS

The invention will be explained herein after in closer detail with reference to some examples and the corresponding figures.

DETAILED DESCRIPTION OF THE INVENTION

Figure 1:
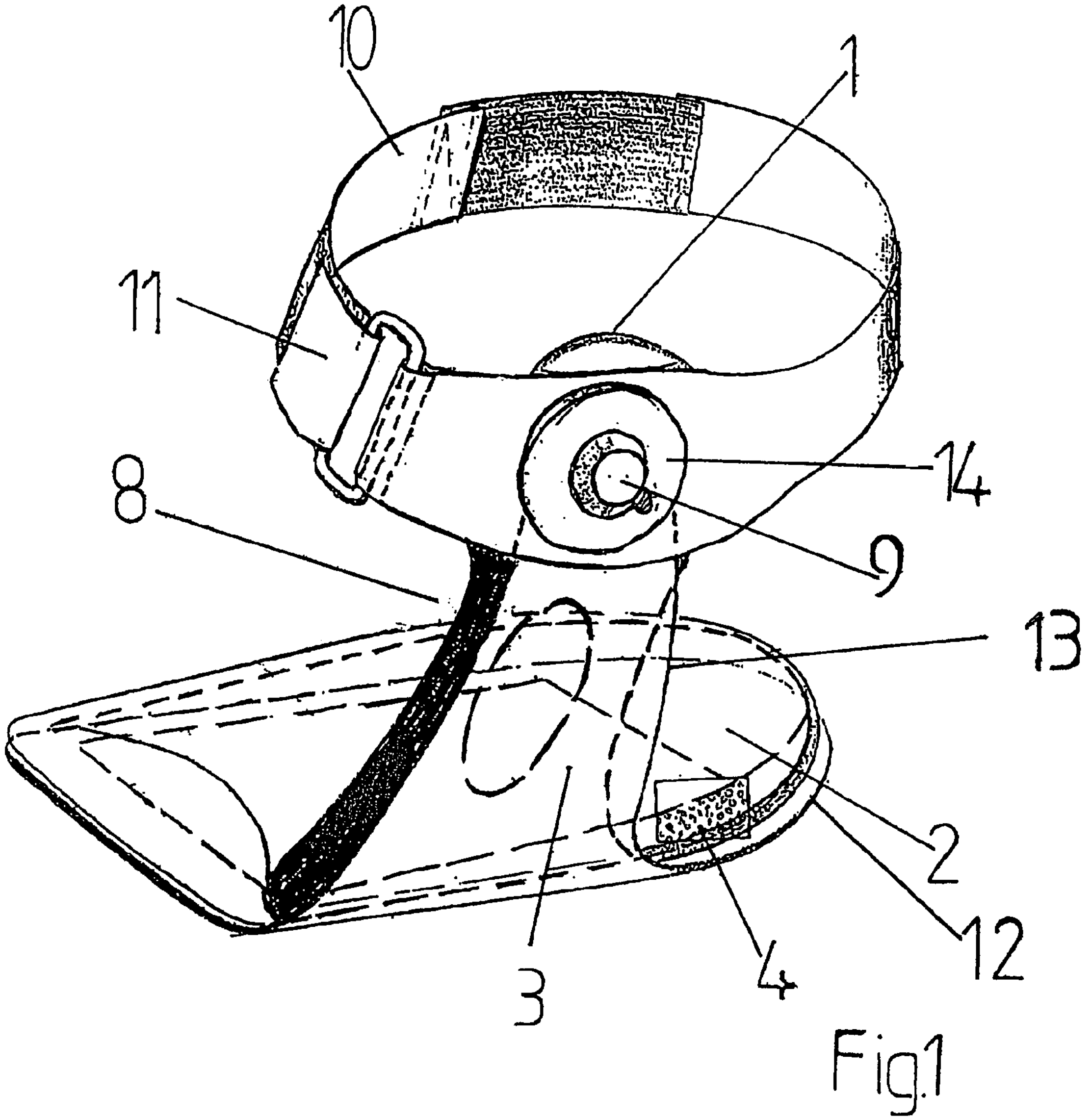
FIG. 1 is a simplified perspective view of a frame with bladder, base pad and tubular connection attached thereon.

FIG. 1 shows an advantageous embodiment of the invention that can be utilized in therapeutic practice. The device according to the invention comprises a bladder arranged in the region of the lower leg. A tubular connection 3 extends between the inner spaces of the base pad 2 and the bladder 1. Furthermore the device comprises a working fluid in the bladder 1 or in the inner spaces of the base pad 2. A frame 8 comprising a base part 12 and at least one side part 13 projects upwardly from the base part 12. The frame 8 can be mounted inside a shoe, wherein the bladder 1 is fastened to the side part 13. The physiologically significant effect is obtained by means of the bladder 1 located above the perforating vein. It is decisive for the success of the therapy that the bladder be located above the location at which the perforating vein emerges beneath the muscles on the rear inner side of the ankle. The desired effect can only be obtained when the bladder is positioned above this location. Positioning is achieved by the individual adjustment of the frame 8 to the respective foot. The bladder 1 is positioned on the frame 8 in such a manner that it covers the lower leg only above a location at which a perforating vein emerges beneath the muscles on the rear inner side of the ankle, so that a person walking while wearing the device will periodically exert a pressure on a pad causing working fluid to inflate the bladder 1 and place periodic pressure just on the location on the leg. Thus the bladder exerts pressure just on very small area of the lower leg, namely, the location at which a perforating vein emerges beneath the muscles on the rear inner side of the ankle. The valve 9, which is located on that side of the bladder which is turned away from the foot, is passed through a bore located in the upper region of side part 13 of frame 8 for keeping the bladder from slipping sideways. Thanks to this realization the bladder 1 is kept in place. Clinical tests showed that the greatest therapeutic benefit is obtained when a rhythmic-dynamic pressure is exerted onto the perforating vein. Pressure is therefore generated through a base pad 2 which is accommodated in the heel area and is compressed by the body weight in the rhythm of the walking movement. For a better regeneration of the base pad 2 when the foot is unloaded, the entire volume area of the pad is filled with a spongious material 4, e.g., an open pore foam with high elasticity. The base pad 4 communicates with bladder 1 via a tubular connecting piece 3 which, in the embodiment shown, is in the form of a wide tube that separates after a few centimeters into two legs prior to combining again. The advantage of the configuration of connecting piece 3 as shown in FIG. 1 is that a recess is thus provided in the ankle area and that the pressure transmitted from base pad 2 to bladder 1 is not exerted onto the ankle. The mounting of the entire device into a shoe is also facilitated by this special configuration of the connecting piece 3. When the foot is unloaded the pressure pad 2 expands and the working volume is displaced from the bladder 1 toward the base pad 2 as a result thereof, thus causing the bladder 1 to collapse. The substance displaced in the system consisting of base pad, connecting piece and bladder is a fluid. In the arrangement shown, the base pad 2 is bonded to the bottom of the frame 8.

In order to optimize the attachment of the support 8 to the foot, a partially elastic tape 10, which is placed around the lower leg, is fastened to the support. The tape is configured in such a manner that it reacts resiliently to the pressure of the veins, avoiding nuisance due to the pressure of swollen veins to the wearer of the device and not preventing the blood from flowing back toward the heart as a result thereof. In the illustration of FIG. 1 it may be adjusted to the various calf diameters by way of a Velcro closure system. However, other closure systems that do not require too much space are also possible.

Figure 2:
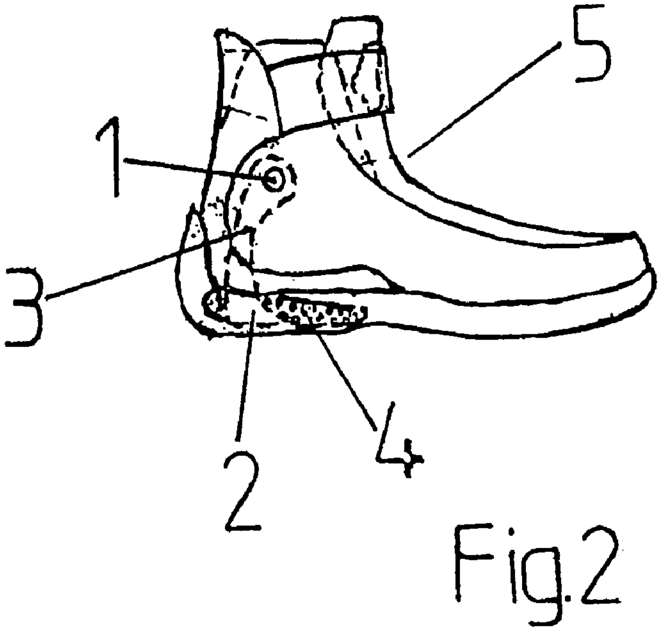
FIG. 2 is a vertical section through the longitudinal axis of a shoe in which a bladder, a base pad and a tubular connection are integrated.

FIG. 2 illustrates a shoe 5 with an integrated therapeutic unit consisting of a base pad in the heel area 2 which is filled with an open pore, elastic material 4, of a bladder 1 placed above the perforating vein and of a tubular connecting piece 3. The integration of the therapeutic unit in a shoe has the advantage that the frame needs not be put on and adjusted and that only the shoe has to be put on. This substantially facilitates the application of the therapeutic unit for infirm patients. When mounting the various elements in the shoe, they are to be positioned individually, according to the respective foot. In many respects it seems indicated to utilize such a shoe when engaging in leisure activities as well. For example during long hikes such as sight-seeing tours for example, the venous system may be aided and fatigue prevented. The venous blood in the legs may also be assisted in flowing back toward the heart on longer flights by wearing such shoes in connection with simple exercises such as arching and relaxing the soles of the feet.

Figure 3:
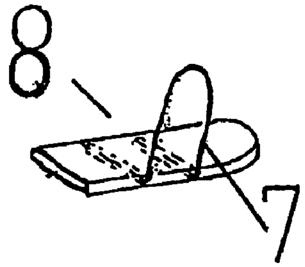
FIG. 3 is a schematic view of a frame with a tiltable bar as shown in FIG. 1; the fastening tape is not illustrated in this FIG.

FIG. 3 shows a frame 8 in which the side part 7 is configured to form a U-shaped bar. The side part 7 may be folded flat against the base part of the frame 8. Through this measure, the transport of the frame is facilitated and it may be readily stowed in a relatively compact space. If, from a therapeutic point of view, the device needs not be worn permanently, it can be easily stowed in a bag and put on when necessary.

Figure 4:
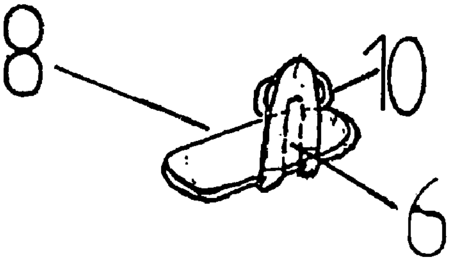
FIG. 4 is a view of a frame as shown in FIG. 3 with bladder, pressure pad and tubular connection attached thereon.

FIG. 4 shows a frame 8 as illustrated in FIG. 3 with bladder 1, base pad 2 and tubular connecting piece 3 attached thereon, a pocket 6 being arranged on those surfaces of bladder 1 and tubular connecting piece 3 that are turned away from the foot, the pocket being capable of receiving the side part 7 configured to form a bar. Bladder 1 and tubular connecting piece 3 are fastened to the frame 8 by the pocket 6 located on the outer surface areas of the two parts in that the pocket 6 is pulled over side part 7. Pocket 6 is constructed in such a manner that the side part 7 completely and closely fits therein. Pocket 6 is made of a tear-resistant, non elastic and foil bondable plastic material. The mounting of the device is substantially facilitated as a result of the just described build. Accordingly, bladder 1, base pad 2 and tubular connecting piece 3 can be transported separately from the frame 8 and easily stowed.

We claim:

1. A device for massaging a lower leg for treating hypostatic leg conditions and for preventing stagnation of blood in the leg comprising a base pad (2) arranged in an area of a sole of a foot and having inner spaces and a bladder (1) arranged in the region of the lower leg, a tubular connection (3) including at least one side part (13) extending between the inner spaces of the base pad (2) and said bladder (1), a working fluid in one of the bladder (1) or the inner spaces of said base pad (2), a frame (8) comprising a base part (12) and said at least one side part (13, 7) projecting upward from said base part (12), said frame (8) being mountable inside a shoe, said bladder (1) being fastened to said side part (13) and said bladder (1) being positioned on said frame (8) in such a manner that it covers the lower leg only above a location at which a perforating vein emerges beneath the muscles on the rear inner side of the ankle, so that a person walking while wearing said device will periodically exert a pressure on the pad (2) causing working fluid to inflate the bladder (1) and place periodic pressure just on said location of the lower leg.

2. A device for massaging a lower leg for treating hypostatic leg conditions and for preventing stagnation of blood in the leg, comprising a base pad (2) having inner spaces and being arranged in an area of a sole of a foot and a bladder (1) arranged in the region of the lower leg, a tubular connection (3) being provided between the inner spaces of the base pad (2) and of the bladder (1), a working fluid in one of the inner spaces of the pad (2) or the bladder (1), said bladder (1) being fastened in the side part of a shoe (5) located on the inner side of the lower leg and the bladder (1) is positioned within the shoe in such a manner that it covers the lower leg only above a location at which a perforating vein emerges beneath the muscles on the rear inner side of the ankle, so that a person wearing the device and while walking will exert a pressure on the pad 2 which will periodically inflate the bladder (1) with the working fluid and place periodic pressure just on said location of the lower leg.

3. The device according to claim 1, wherein a resilient space holder (4) is enclosed within the base pad (2), said space holder expands the inner spaces of the base pad (2) when the foot is unloaded, causing the bladder (1) to collapse correlative to the expansion of said inner spaces of the base pad (2).

4. The device according to claim 3, wherein the resilient space holder is made of open pore foam.

5. The device according to claim 1, wherein the bladder (1), the base pad (2) and the tubular connection (3) located therebetween are made in one piece.

6. The device according to claim 5, wherein a pocket (6) is arranged on one of the bladder (1) or on the tubular connection (3) or on the surfaces thereof that are turned away from the foot, said pocket being capable of receiving the side part (7).

7. The device according to claim 1, wherein the side part (7) is configured to form a U-shaped bar extending upward from the base part.

8. The device according to claim 1, wherein the side part (7) is foldable.

9. The device according to claim 1, wherein a fluid may be allowed to enter and/or exit the bladder (1), the base pad (2) and the tubular connection (3) through a valve (9) located on a side of the bladder (1) turned away from the foot.

10. The device according to claim 3, wherein a bore (14) for receiving a valve (9) and, as a result thereof, for fixating the bladder (1) on the frame (8), is provided in an upper region of the side part (7).

11. The device according to claim 1, wherein the bladder (1), the base pad (2) and the tubular connection (3) therebetween are made of a foil bondable plastic material.

12. The device according to claim 3, wherein the frame (8) is provided with an elastic tape (10) which is arranged in the upper region of the side part (7) and is fastenable to the lower leg by means of a closure.

* * * * *